US009291505B2

(12) United States Patent
Childers et al.

(10) Patent No.: US 9,291,505 B2
(45) Date of Patent: Mar. 22, 2016

(54) POLARIZATION SCRAMBLING IN INTERFEROMETER SYSTEMS

(71) Applicants: Brooks A. Childers, Christiansburg, VA (US); Roger Glen Duncan, Christiansburg, VA (US); Ajit Balagopal, Christiansburg, VA (US); Dan R. Provenzano, Blacksburg, VA (US)

(72) Inventors: Brooks A. Childers, Christiansburg, VA (US); Roger Glen Duncan, Christiansburg, VA (US); Ajit Balagopal, Christiansburg, VA (US); Dan R. Provenzano, Blacksburg, VA (US)

(73) Assignee: BAKER HUGHES INCORPORATED, Houston, TX (US)

( * ) Notice: Subject to any disclaimer, the term of this patent is extended or adjusted under 35 U.S.C. 154(b) by 144 days.

(21) Appl. No.: 13/707,979

(22) Filed: Dec. 7, 2012

(65) Prior Publication Data

US 2014/0160483 A1  Jun. 12, 2014

(51) Int. Cl.
*G01B 9/02* (2006.01)
*G01J 4/00* (2006.01)
*G01N 21/954* (2006.01)
*G01D 5/353* (2006.01)

(52) U.S. Cl.
CPC .............. *G01J 4/00* (2013.01); *G01D 5/35316* (2013.01); *G01D 5/35393* (2013.01); *G01N 21/954* (2013.01)

(58) Field of Classification Search
CPC .......... G01D 5/35383; G01D 5/35303; G01D 5/353; G01H 9/004; G01B 9/02
USPC ........................................................ 356/478
See application file for complete search history.

(56) References Cited

U.S. PATENT DOCUMENTS

| 5,104,222 | A | 4/1992 | Kersey et al. | |
|---|---|---|---|---|
| 6,856,401 | B1 | 2/2005 | Ronnekleiv | |
| 2002/0093662 | A1* | 7/2002 | Chen et al. | 356/491 |
| 2003/0035120 | A1* | 2/2003 | Myatt et al. | 356/519 |
| 2003/0223073 | A1* | 12/2003 | VanWiggeren et al. | 356/477 |
| 2004/0264981 | A1* | 12/2004 | Zhang et al. | 398/204 |
| 2005/0047706 | A1* | 3/2005 | Waagaard et al. | 385/11 |
| 2005/0129346 | A1* | 6/2005 | Chen et al. | 385/11 |
| 2006/0088259 | A1* | 4/2006 | Weiner | 385/122 |
| 2006/0114471 | A1* | 6/2006 | Cyr | 356/477 |
| 2007/0051882 | A1 | 3/2007 | Childers | |
| 2008/0221837 | A1* | 9/2008 | De Groot | 702/189 |
| 2009/0073453 | A1* | 3/2009 | Hasegawa | 356/477 |
| 2009/0185810 | A1* | 7/2009 | Kaplan et al. | 398/184 |
| 2009/0207416 | A1* | 8/2009 | Xiangqian | G01B 11/2441 356/477 |
| 2010/0128278 | A1* | 5/2010 | Deck et al. | 356/477 |
| 2010/0271623 | A1* | 10/2010 | Cranch | G01D 5/35303 356/73.1 |
| 2012/0297883 | A1 | 11/2012 | Kupershmidt | |

OTHER PUBLICATIONS

General Photonics Corporation, "Scrambling to Reduce Polarization Related Impairments" Apr. 2003, pp. 1-4.
International Search Report and Written Opinion for PCT Application No. PCT/US2013/068068, dated Jan. 24, 2014, pp. 1-9.

* cited by examiner

*Primary Examiner* — Tarifur Chowdhury
*Assistant Examiner* — Md Rahman
(74) *Attorney, Agent, or Firm* — Cantor Colburn LLP

(57) ABSTRACT

A system and method to obtain and process interferometer output scans is described. The interferometer-based sensor system includes a tunable laser to transmit a transmit signal and a polarization scrambler to produce a polarization state change on the transmit signal. The system also includes an interferometer to provide an output scan based on the transmit signal with the polarization state change and a processor to process the output scan.

12 Claims, 4 Drawing Sheets

POLARIZATION SCRAMBLING IN INTERFEROMETER SYSTEMS

BACKGROUND

In downhole exploration and geologic resource recovery, the ability to obtain information about the conditions of the environment and the status of the equipment downhole can be helpful in making decisions. Optical frequency domain reflectometers (OFDR) are among the types of sensors used downhole. OFDR is an interferometer-based system that relies on the interference between signals generated or reflected by individual sources based on an optical signal. When the polarizations of the two signals are parallel to each other (0 degree angle between them), this provides maximum interference. However, when the two signals have orthogonal polarizations (90 degree angle between them), then there is no interference between the signals and, as a result, no signal from the interferometer. This results in noisy output from the OFDR system, which cannot know when the interferometer signal is null. Thus, an apparatus and method to ensure performance of the interferometer-based systems would be appreciated in the industry.

SUMMARY

According to one aspect of the invention, an interferometer-based sensor system includes a tunable laser configured to transmit a transmit signal; a polarization scrambler configured to produce a polarization state change on the transmit signal; an interferometer configured to provide an output scan based on the transmit signal with the polarization state change; and a processor configured to process the output scan.

According to another aspect of the invention, a method of obtaining and processing interferometer output scans includes arranging a polarization scrambler between a tunable laser and an interferometer; changing a polarization state of each signal from the tunable laser with the polarization scrambler to generate each polarization scrambled signal; receiving each of the output scans from the interferometer based on each of the polarization scrambled signals; and processing the output scans.

BRIEF DESCRIPTION OF THE DRAWINGS

Referring now to the drawings wherein like elements are numbered alike in the several Figures.

DETAILED DESCRIPTION

Any interferometer-based sensor system (e.g., optical frequency domain reflectometer (OFDR)) relies on the interference among signals generated or reflected by individual sources to generate the interferometer signal used to determine information of interest. Embodiments of the invention described herein ensure reliable interferometer signals for accurate measurements. While OFDR systems are used as exemplary interferometer-based systems for purposes of explanation, the scrambler and scrambling method detailed below applies, as well, to other interferometer-based systems.

Figure 1:
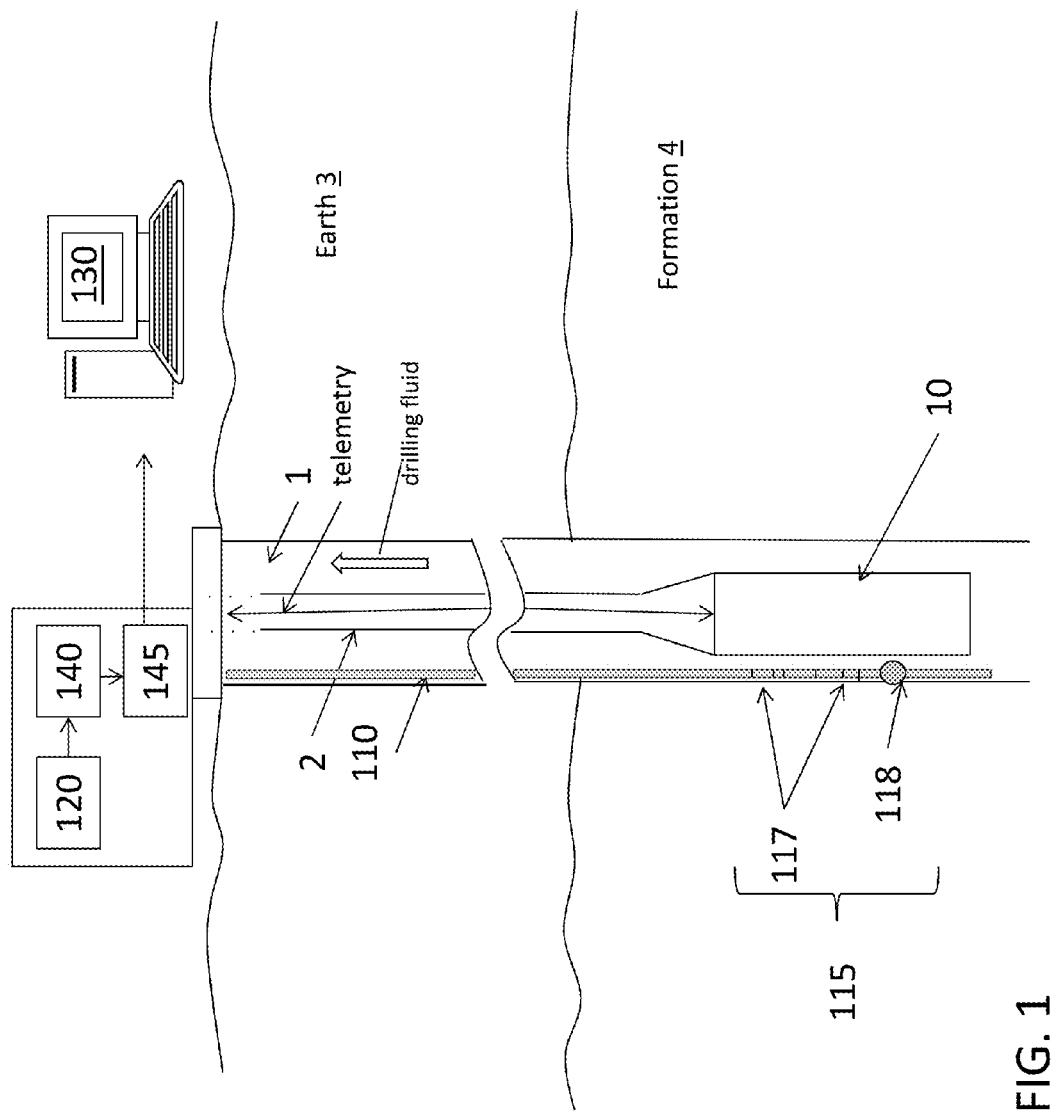
FIG. 1 is a cross-sectional illustration of a borehole including a distributed acoustic sensor system according to an embodiment of the invention.

FIG. 1 is a cross-sectional illustration of a borehole 1 including an interferometer-based sensor system according to an embodiment of the invention. A borehole 1 penetrates the earth 3 including a formation 4. A set of tools 10 may be lowered into the borehole by a carrier 2. In embodiments of the invention, the carrier may be an armored wireline. In measure-while-drilling (MWD) embodiments, the carrier 2 may be a drill string, and a drill would be included below the tools 10. Information from the sensors and measurement devices included in the set of tools 10 may be telemetered to the surface for processing by the surface processing system 130. The interferometer-based sensor system includes an optical fiber 110. In the exemplary embodiment shown in FIG. 1, the optical fiber 110 includes fiber Bragg gratings (FBGs) 117 and a reference reflector 118 that comprise an interferometer 115. A tunable laser 120 is shown at the surface of the earth 3 in FIG. 1. The polarization scrambler 140 that acts on the tunable laser 120 output before the optical network 145 transmits the signal to the interferometer 115 is discussed in detail with reference to FIG. 2 below.

Figure 2:
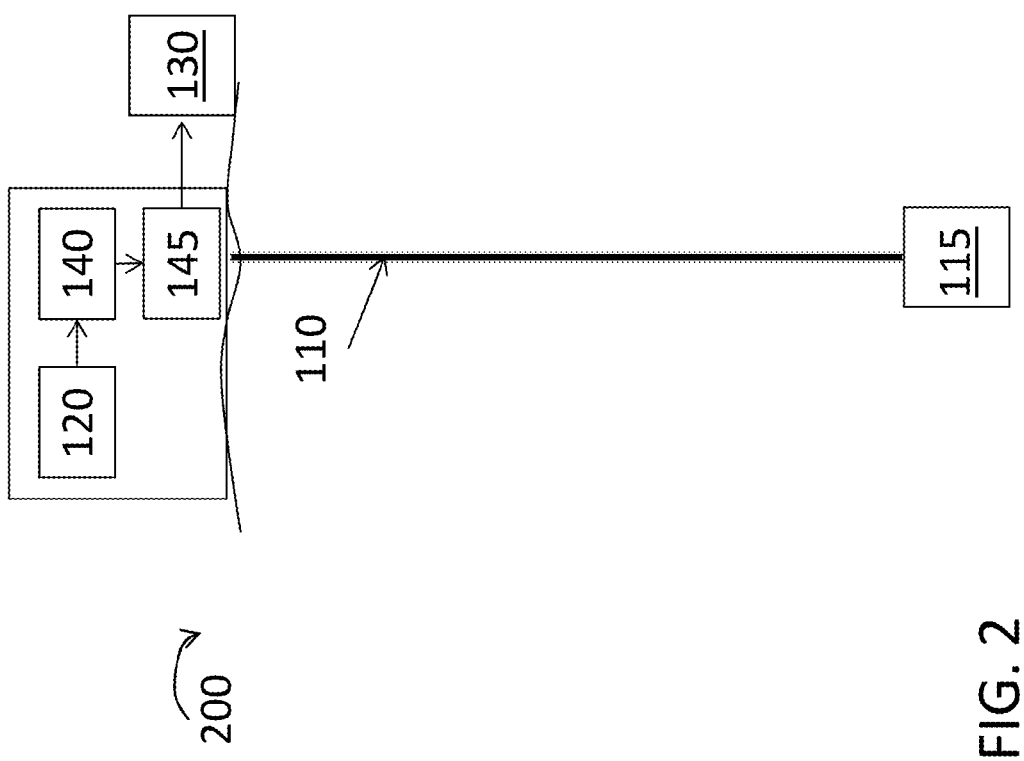
FIG. 2 is a block diagram of an OFDR network including a polarization scrambler according to an embodiment of the invention.

FIG. 2 is a block diagram of an OFDR network 200 including a polarization scrambler 140 according to an embodiment of the invention. The polarization scrambler 140 acts on the signal from the tunable laser 120 being sent to the interferometer 115. By varying the polarization state of the signal input to the interferometer 115, a higher percentage of non-null interferometer signals (signals not being perpendicular to each other) are ensured as interferometer output. The output of the tunable laser 120 may itself have a different polarization state over time. However, this variation in the signal from the tunable laser 120 is not certain or predictable. The polarization scrambler 140, unlike the tunable laser 120, can be made to randomly vary the polarization state of the tunable laser 120 output over time before it reaches the interferometer. The possible polarization states achieved by the polarization scrambler 140 may be mapped over time and would indicate uniform sampling that could be represented by a Poincaré sphere, for example. Even though the tunable laser 120 changes polarization states over time, it would not achieve this uniform sampling of polarization states. In alternate embodiments, the polarization scrambler 140 may change polarization state of the tunable laser 120 output in a predefined pattern.

Figure 3:
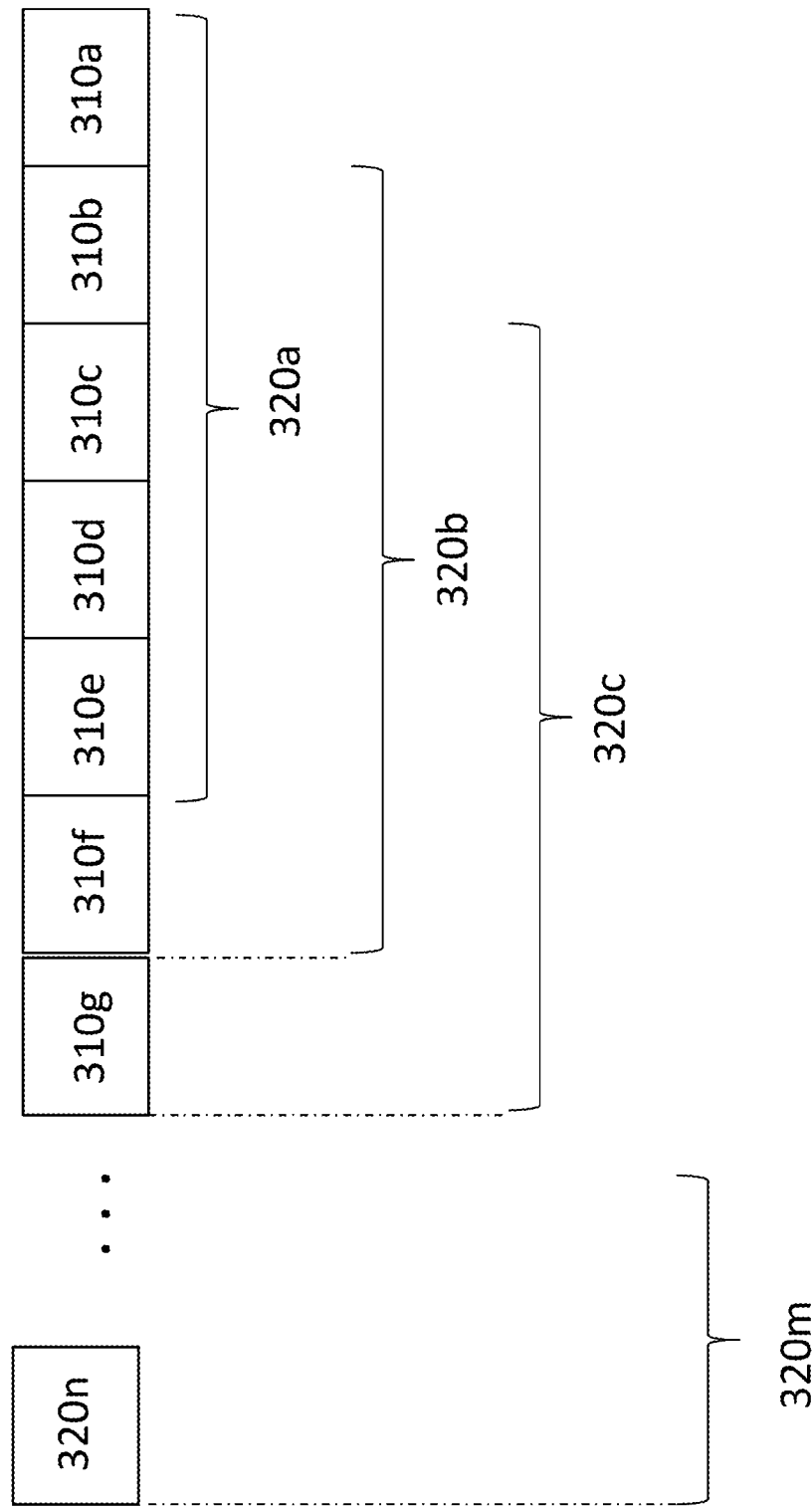
FIG. 3 illustrates an exemplary processing scheme for the OFDR network shown in FIG. 2 according to an embodiment of the invention.

FIG. 3 illustrates an exemplary processing scheme for the OFDR network 200 shown in FIG. 2 according to an embodiment of the invention. The polarization state of the tunable laser 120 output is randomly varied prior to each scan. The output 310 of the interferometer 115 for each scan is averaged over a number of scans. In the embodiment shown in FIG. 3, 5 outputs 310 (the result of 5 scans of the tunable laser 120 randomly varied in polarization state by the polarization scrambler 140) are averaged at a time in a sliding window fashion. That is, the first 5 outputs 310a-310e are averaged as 320a, then the first scan 310a is dropped and the next scan 310f is included in the next average 320b. The sliding window average continues in this fashion. The average may be a weighted average such that larger amplitude interferometer 115 outputs 310 are weighted higher than lower amplitude outputs 310. Weighting may be based on other factors like signal-to-noise ratio, for example. The averaging increases the signal-to-noise ratio (SNR) of the interferometer 115 output 310. In alternate embodiments, the exemplary processing shown by FIG. 3 may be varied in one or more ways. For example, a different number of outputs 310 may be averaged at a time or a different weighting scheme may be used for the outputs 310 to provide the weighted average 320.

Figure 4:
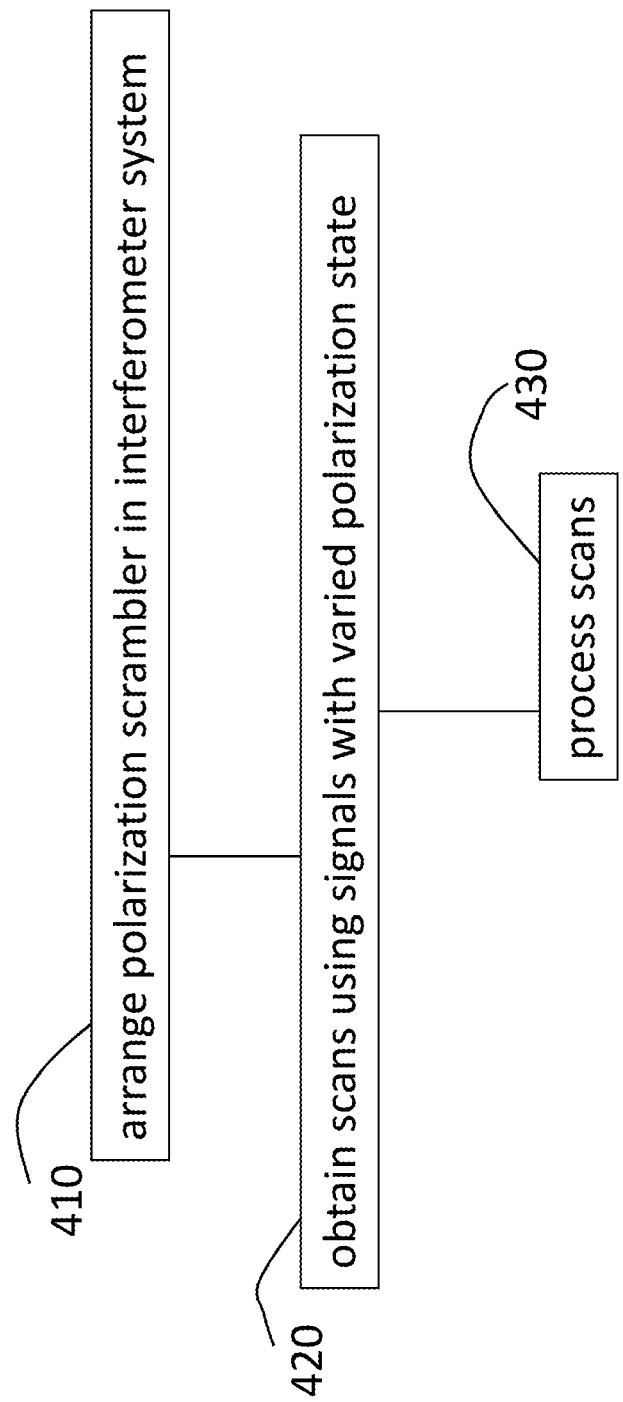
FIG. 4 is a process flow diagram of an exemplary method 400 to obtain interferometer output using polarization scrambling according to embodiments of the invention.

FIG. 4 is a process flow diagram of an exemplary method 400 to obtain interferometer output using polarization scrambling according to embodiments of the invention. At block 410, arranging the polarization scrambler 140 in the interferometer system may include, for example, arranging the polarization scrambler 140 between the tunable laser 120 and the interferometer 115 as shown in FIG. 2 for the exemplary OFDR network 200. Obtaining scans using signals with varied polarization state at block 420 includes the polarization scrambler 140 randomly or in a predefined pattern changing the polarization state of the tunable laser 120 output. Block 420 also includes receiving the resulting interferometer 115 output scans. Processing the scans at block 430 may include, for example, weighting and averaging a particular number of interferometer 115 output scans at a time in a sliding window fashion, as discussed with reference to FIG. 3.

While one or more embodiments have been shown and described, modifications and substitutions may be made thereto without departing from the spirit and scope of the invention. Accordingly, it is to be understood that the present invention has been described by way of illustrations and not limitation.

The invention claimed is:

1. An interferometer-based sensor system, comprising:
a tunable laser configured to transmit a transmit signal;
a polarization scrambler configured to change a polarization state of the transmit signal prior to each scan such that the polarization state of the transmit signal for one scan differs from the polarization state of the transmit signal for another scan;
an interferometer configured to provide an output scan based on the transmit signal with the polarization state change for each scan, the interferometer comprising one or more fiber Bragg gratings (FBGs) and a reference reflector and the output scan resulting from interference between a reflection signal from the reference reflector with a reflection signal from one of the one or more FBGs; and
a processor configured to process the output scan.

2. The system according to claim 1, wherein the polarization state change is random, and, over a period of time, polarization states are uniform.

3. The system according to claim 1, wherein the processor processes a number of the output scans at a time, the number being received over a period of time.

4. The system according to claim 3, wherein the processor performs a weighted average on the number of the output scans, each weighting being based on an amplitude of the respective output scan.

5. The system according to claim 3, wherein the processor performs a weighted average on the number of output scans, each weighting being based on a signal-to-noise ratio of the respective output scan.

6. The system according to claim 3, wherein the processor uses a sliding window to select the number of the output scans.

7. A method of obtaining and processing interferometer output scans, the method comprising:
arranging a polarization scrambler between a tunable laser and an interferometer, the interferometer comprising one or more fiber Bragg gratings (FBGs) and a reference reflector;
changing a polarization state of each signal from the tunable laser with the polarization scrambler prior to each scan to generate each polarization scrambled signal, the polarization state of one of the polarization scrambled signals being different from the polarization state of another of the polarization scrambled signals;
receiving each of the output scans from the interferometer based on each of the polarization scrambled signals for each scan, each of the output scans resulting from interference between a reflection signal from the reference reflector with a reflection signal from one of the one or more FBGs; and
processing the output scans.

8. The method according to claim 7, wherein the changing the polarization state includes generating a uniform sampling of polarization states over time.

9. The method according to claim 7, wherein the processing the output scans includes determining a weighted average of a number of the output scans.

10. The method according to claim 9, wherein the determining the weighted average includes weighting each of the output scans of the number of the output scans based on an amplitude of the respective output scan.

11. The method according to claim 9, wherein the determining the weighted average is done in a sliding window fashion with one of the number of the output scans being different in each of the weighed averages.

12. The method according to claim 9, wherein the determining the weighted average includes weighting each of the output scans of the number of the output scans based on a signal-to-noise ratio of the respective output scan.

* * * * *